(12) United States Patent
Boettcher et al.

(10) Patent No.: US 10,112,162 B2
(45) Date of Patent: Oct. 30, 2018

(54) METHODS OF MIXING IMPELLER SENSING

(71) Applicants: Sartorius Stedim Biotech GmbH, Goettingen (DE); Jonathan E. Cutting, East Setauket, NY (US)

(72) Inventors: Lars Boettcher, Melsungen (DE); Jonathan E. Cutting, East Setauket, NY (US); Sharon D. West, Sunnyside, NY (US); Martin Oschwald, Tagelswangen (CH)

(73) Assignees: Sartorius Stedim Biotech GmbH, Goettingen (DE); Jonathan E. Cutting, East Setauket, NY (US)

(*) Notice: Subject to any disclaimer, the term of this patent is extended or adjusted under 35 U.S.C. 154(b) by 454 days.

(21) Appl. No.: 15/010,317

(22) Filed: Jan. 29, 2016

(65) Prior Publication Data
US 2017/0216798 A1   Aug. 3, 2017

(51) Int. Cl.
| | |
|---|---|
| *B01F 15/00* | (2006.01) |
| *B01F 3/12* | (2006.01) |
| *B01F 13/08* | (2006.01) |
| *G01N 11/14* | (2006.01) |
| *B01F 7/18* | (2006.01) |
| *C12M 1/02* | (2006.01) |
| *G01N 1/38* | (2006.01) |
| *G01N 11/00* | (2006.01) |

(52) U.S. Cl.
CPC ...... *B01F 15/00285* (2013.01); *B01F 3/1221* (2013.01); *B01F 13/0818* (2013.01); *B01F 15/00201* (2013.01); *B01F 15/00233* (2013.01); *B01F 15/00246* (2013.01); *B01F 15/00389* (2013.01); *G01N 11/14* (2013.01); *B01F 7/18* (2013.01); *B01F 2215/0032* (2013.01); *B01F 2215/0463* (2013.01); *B01F 2215/0481* (2013.01); *C12M 27/00* (2013.01); *G01N 2001/386* (2013.01); *G01N 2011/0006* (2013.01); *G01N 2011/0026* (2013.01); *G01N 2011/0053* (2013.01)

(58) Field of Classification Search
CPC .................................................. B01F 15/00285
See application file for complete search history.

(56) References Cited

U.S. PATENT DOCUMENTS

| | | | | | |
|---|---|---|---|---|---|
| 4,548,765 | A | * | 10/1985 | Hultholm | B01F 7/00466 209/169 |
| 4,594,883 | A | * | 6/1986 | Pollard | B01F 15/00201 73/54.23 |
| 6,395,516 | B1 | * | 5/2002 | Nienow | B01F 7/00158 366/318 |
| 9,702,800 | B2 | * | 7/2017 | Morgan | G01N 11/14 |
| 2013/0118235 | A1 | * | 5/2013 | Morgan | G01N 11/14 73/54.28 |
| 2016/0047184 | A1 | * | 2/2016 | Luharuka | B01F 15/00201 166/250.01 |

* cited by examiner

*Primary Examiner* — Abbas Rashid
(74) *Attorney, Agent, or Firm* — Gerald E. Hespos; Michael J. Porco; Matthew T. Hespos (57) ABSTRACT

A method is provided for monitoring a flow behavior of mixed components without requiring additional instrumentation or sampling. The method is carried out by determining ratios of the power required to rotate a mixing impeller at different rotational speeds and then comparing the ratios. Characteristics about the mixed components are determined based on differences between the ratios.

5 Claims, 5 Drawing Sheets

METHODS OF MIXING IMPELLER SENSING

BACKGROUND

1. Field of the Invention

The invention relates to a method of monitoring a flow behaviour of components to be mixed, a control system and methods for detecting settled solids at a mixing impeller.

2. Related Art

Biopharmaceutical manufacturing requires mixing at several process steps, for example media preparation, buffer preparation, low pH viral inactivation of material between process steps. For this mixing step, usually the components to be mixed are accommodated in a mixing vessel in which a mixing impeller is provided. The mixing impeller is driven by a motor so that the mixing impeller is rotated. The mixing impeller usually comprises a rotationally symmetric mixing impeller basis and at least one mixing impeller blade that is attached to the mixing impeller basis. The mixing impeller blade extends radially or axially with respect to a rotation axis from the mixing impeller basis. The geometry and size of the mixing blade are chosen depending on the mixing application. For example, the mixing blade may be straight, curved and/or backswept with respect to the rotation axis of the mixing impeller.

The mixing vessel may be a rigid or flexible container. A rigid mixing vessel is used mostly as a reusable container, while flexible mixing vessels are used mostly as a single-use container.

The mixing impeller inside of the mixing vessel may be connected to the motor via a driving shaft that extends through the mixing vessel side wall. However, some applications require that the mixing equipment is fully closed with no possibility of leakage between the mixing vessel and the environment—for example, the fluids to be mixed are either hazardous (e.g. toxic) or if they are sensitive to contamination from the outside environment (e.g. highly purified pharmaceutical material). In such cases, a magnet drive system may be employed as a means of transmitting torque between an external motor and a mixing impeller inside of the mixing vessel. A driving magnet at the outside of the mixing vessel is driven by the external motor, and a follower magnet is arranged inside of the mixing impeller in the mixing vessel.

In contrast to the conventional mixing equipment, in which mixing vessels typically are fabricated from stainless steel or other alloys, single-use systems comprise plastic bags as mixing vessels and are used only once. Single-use systems are used increasingly in biopharmaceutical manufacturing operations because of the increased flexibility, lower capital cost, elimination of cleaning steps, reduced risk of cross-contamination, and reduced utility burden.

When mixing two or more components in a mixing vessel (e.g. liquid-liquid, liquid-solid), there may be a desired viscosity or density of the components to be mixed. Alternatively, there could be a viscosity or density range that is to be avoided.

Therefore, a method is required that allows the determination of the density and viscosity of the components to be mixed without requiring additional instrumentation or sampling so that the density and viscosity of the components to be mixed are monitored.

SUMMARY

According to an aspect of this disclosure, this underlying technical problem has been solved by a method of monitoring a flow behavior of mixed components, comprising:

rotating a mixing impeller at a first speed $N_1$ in a mixing vessel accommodating the components to be mixed; determining a first quantity $$\frac{P_1}{N_1^3}$$

at the first speed $N_1$, wherein $N_1$ is the speed at which the mixing impeller rotates and $P_1$ is the power required to rotate the mixing impeller at the first speed $N_1$;

decreasing the speed of the mixing impeller to a speed $N_2$; determining a second quantity $$\frac{P_2}{N_2^3}$$

at the second speed $N_2$, wherein $N_2$ is the speed at which the mixing impeller rotates and $P_2$ is the power required to rotate the mixing impeller at the second speed $N_2$;

comparing the first quantity $$\frac{P_1}{N_1^3}$$

and the second quantity $$\frac{P_2}{N_2^3}$$

and detecting whether the difference between the first and second quantities is within a specified range to determine whether the flow of the components in the mixing vessel is a turbulent flow;

determining the density $\rho$ of the mixed components based on at least one speed $N_i$ for which the flow is determined to be turbulent by the following formula:

$$\rho = \frac{P_i}{N_{P,constant} N_i^3 D^5}$$

wherein $\rho$ is the density, $P_i$ is the power required to turn the mixing impeller at the speed $N_i$, $N_{P,constant}$ is the Power number for a used mixing system configuration, $N_1$ is the speed at which the mixing impeller rotates and $D$ is the diameter of the mixing impeller;

further decreasing the speed of the mixing impeller;

determining the Power number $N_{P,variable}$ for at least one detected speed $N_j$ at which the flow is determined to be non-turbulent by the following formula:

$$N_{P,variable} = \frac{P_j}{\rho N_j^3 D^5}$$

wherein $P_j$ is the power required to rotate the mixing impeller at the speed $N_j$, $\rho$ is the density previously determined based on $N_{P,constant}$, $N_j$ is the speed at which the mixing impeller rotates, and $D$ is the diameter of the mixing impeller; and determining the dynamic viscosity μ of the mixed components by the following formula:

$$\mu = \frac{\rho^2 N_j^5 D^6}{x_T P_j}$$

wherein ρ is the calculated density, $N_j$ is the speed at which the mixing impeller rotates, D is the diameter of the mixing impeller, $P_j$ is the power required to rotate the mixing impeller at the speed $N_j$ and $x_T$ corresponds to a specified relationship between the Reynolds number for the used mixing system configuration and the determined Power number $N_{P,variable}$.

A "first speed" of the mixing impeller corresponds to a starting speed at which the mixing impeller rotates. Preferably, the "first speed" is the highest speed at which the mixing impeller rotates during the described method. Alternatively, the "first speed" refers to the first speed at which the first quantity $$\frac{P_1}{N_1^3}$$

is determined.

A "second speed" of the mixing impeller corresponds to speed to which the mixing impeller has been reduced after rotating at the first speed. Alternatively, the "second speed" refers to the second speed at which the second quantity $$\frac{P_2}{N_2^3}$$

is determined.

The threshold that should not be exceeded when comparing the first and second quantities so that a flow of the mixed components shall be considered as turbulent is specified. In this respect, e.g. the operator may determine this threshold in a control system based on his knowledge about acceptable variations in the quantities.

Any parameters that are indicated by the index i, like e.g. the speed $N_i$, shall refer to the range where the flow of the mixed components is considered to be turbulent. Any parameter, however, that is indicated by the index j, like e.g. the speed $N_j$, shall refer to the range where the flow of the mixed components is considered to be non-turbulent. When referring to e.g. the speed of the mixing impeller, index i implies that the speed $N_i$ is higher than the speed $N_j$.

The parameter "$N_{p,constant}$" refers to a range where the Power number $N_P$ is substantially constant when considered in relation to the Reynolds number $N_{Re}$, which will be described in detail below. In this range, the flow of the mixed components is considered to be turbulent.

The parameter "$N_{p,variable}$" refers to a range where the Power number $N_P$ is variable and substantially inconstant when considered in relation to the Reynolds number $N_{Re}$, which will be described in detail below. In this range, the flow of the mixed components is considered to be non-turbulent.

It should be understood that the parameter $x_T$ particularly may take different values for different Reynolds numbers $N_{Re}$ e.g. $x_T$ may take a value of approximately 0 when the flow is substantially turbulent (i.e. the Power number $N_{p,constant}$ will be constant for different Reynolds numbers $N_{Re}$, may be substantially constant for a laminar flow (i.e. for small Reynolds numbers $N_{Re}$, and may be variable (i.e. $x_T$=function($N_{Re}$)) for a transition region.

The described method uses the relationship between the Reynolds number $N_{Re}$ and the Power number $N_P$, which is typical for each single mixing system geometry, for determining the density ρ and the dynamic viscosity μ of the mixed components. No further instrumentations or sampling are needed so that the method can be realized in a simple and inexpensive manner.

The current speed $N_i$ may be reduced iteratively to a speed $N_{i+1}$ and the quantity $$\frac{P_{i+1}}{N_{i+1}^3}$$

is determined iteratively at the respective speed $N_{i+1}$ as long as a turbulent flow is determined when comparing the determined quantity $$\frac{P_{i+1}}{N_{i+1}^3}$$

with the previously determined quantity $$\frac{P_i}{N_i^3}.$$

This means that the density is not necessarily determined after a difference has been determined between the first quantity $$\frac{P_1}{N_1^3}$$

and the second quantity $$\frac{P_2}{N_2^3}.$$

If the difference between the first and second quantities is within a specified range, then the flow is considered to be turbulent. In this case, the speed is further reduced and a further quantity is determined at this reduced speed. This further quantity is compared again with the previously determined quantity (here: the second quantity). Only if this difference exceeds the specified range then the density is determined (at a speed N where the flow is determined to be turbulent). Otherwise, the speed is reduced further. In other words, the speed reduction, the determination of the quantity $$\frac{P_i}{N_i^3}$$

and the determination of the difference between the previously determined quantity $$\frac{P_{i+1}}{N_{i+1}^3}$$

and the currently determined quantity is repeated as long as turbulent flow is detected.

Preferably, the average density $\bar{\rho}$ may be calculated based on plural densities $\rho_i$ determined for plural speeds $N_i$ for which the flow is determined to be turbulent.

When an average of the densities is determined, any variations which might apply during the method could be compensated. The value of the determined density would be more accurate.

The speed $N_i$ of the mixing impeller may be reduced in steps and the speed $N_i$ is maintained for a specified time $t_{stab}$ so that a flow pattern is able to stabilize at each so speed.

The time $t_{stab}$ for which the speed is maintained may be constant over the whole described method. Alternatively, the time $t_{stab}$ may be identical for the time where the flow of the components to be mixed is considered to be turbulent, and/or the time $t_{stab}$ may be identical for the time where the flow of the $t_{stab}$ components to be mixed is no longer considered to be turbulent. Alternatively, the time $t_{stab}$ may differ at least partly for the various speeds $N_i$ and/or $N_j$.

The time $t_{stab}$ may be a specified time. Preferably, the time $t_{stab}$ may be based on the experience of the operator after which term usually a flow pattern has been stabilized. The time $t_{stab}$ may be stored in a control system.

The method may further comprise the step of outputting the determined density $\rho$ and the dynamic viscosity $\mu$. For example, the values may be outputted to a display to be displayed. Thus, the operator may be informed about the density $\rho$ and the dynamic viscosity $\mu$. Alternatively or additionally, an alert may be sent to the operator if any of the calculated parameters is not within a determined range, the data may be sent to a supervisory control and data acquisition (SCADA system) or historian.

According to another aspect of the disclosure, the underlying technical problem has been solved by a control system for monitoring a flow behaviour of mixed components, comprising:
- a memory for storing a relationship between a Reynolds number $N_{Re}$ and a Power number $N_p$ for at least one used mixing system geometry;
- an input means adapted to receive data regarding at least one of the speed N of the mixing impeller and the power P required to rotate the mixing impeller;
- a speed control means which is adapted to control the speed of the mixing impeller;
- a determining means which is adapted to:
  determine a quantity $$\frac{P_i}{N_i^3}$$

at various speeds $N_i$ of the mixing impeller and compare two subsequently calculated quantities in order to determine whether the difference is within a specified range to determine whether the flow of the components in the mixing vessel is a turbulent flow, wherein $N_i$ is the speed at which the mixing impeller rotates and $P_i$ is the power required to rotate the mixing impeller at the speed $N_i$;

determine the density $\rho$ of the mixed components based on at least one speed $N_i$ for which the flow is determined to be turbulent by the following formula:

$$\rho = \frac{P_i}{N_{P,constant} N_i^3 D^5}$$

wherein $\rho$ is the density, $P_i$ is the power required to turn the mixing impeller at the speed $N_i$, $N_{P,constant}$ is the Power number for a used mixing system configuration, $N_i$ is the speed at which the mixing impeller rotates and D is the diameter of the mixing impeller;

determine the Power number $N_{P,variable}$ for at least one detected speed $N_j$ at which the flow is determined to be non-turbulent by the following formula:

$$N_{P,variable} = \frac{P_j}{\rho N_j^3 D^5}$$

wherein $P_j$ is the power required to rotate the mixing impeller at the speed $N_j$, $\rho$ is the density previously determined based on $N_{P,constant}$, $N_j$ is the speed at which the mixing impeller rotates, and D is the diameter of the mixing impeller; and to determine the dynamic viscosity $\mu$ of the mixed components by the following formula:

$$\mu = \frac{\rho^2 N_j^5 D^6}{x_T P_j}$$

wherein $\rho$ is the calculated density, $N_j$ is the speed at which the mixing impeller rotates, D is the diameter of the mixing impeller, $P_j$ is the power required to rotate the mixing impeller at the speed $N_j$ and $x_T$ corresponds to a specified relationship between the Reynolds number for the used mixing system configuration and the determined Power number $N_{P,variable}$.

The speed control means may be adapted to reduce the speed of the mixing impeller in steps and the speed is maintained for a specified time $t_{stab}$ so that a flow pattern is able to stabilize at each speed.

Further, the control system may further comprise an output means for outputting the calculated density $\rho$ and the dynamic viscosity $\mu$.

According to another aspect, in solid-liquid operations a powdered or granulated solid is added to a liquid and mixed in a mixing vessel. The solid may dissolve in the liquid (e.g. potassium chloride in water) or it may be insoluble and suspended (e.g. diatomaceous earth in water). Although the solids are typically added to the liquid while the mixing impeller is rotating, there are situations in which the mixing impeller may be partially or fully obstructed by solid, like e.g. powder. In this case, the mixing impeller is at least partly inoperable and damages may occur at the mixing impeller, the mixing vessel and/or the motor driving the mixing impeller.

Therefore, it is the underlying technical problem to provide a method for detecting solids at a mixing impeller which might block the mixing impeller and causes damages to the mixing system.

According to an aspect of this disclosure, this underlying technical problem has been solved by a method for detecting settled solids at a mixing impeller, comprising:
providing the mixing impeller in a mixing vessel;

accommodating components to be mixed in the mixing vessel;

rotating the mixing impeller at a speed $N_{start}$ for a time $t_{start}$, wherein the speed $N_{start}$ is lower than the speed at which the mixing impeller is mixing components;

detecting whether an overload of a motor driving the mixing impeller applies during time$_{start}$;

detecting a torque required to rotate the mixing impeller at the speed $N_{start}$ and comparing the detected torque with a known torque required to rotate the mixing impeller in the absence of solids;

determining that the mixing impeller is blocked by solids if at least one of overload or a higher torque is detected.

This method is generally applicable so that the method can be used for any kind of mixing impeller, mixing vessel and connection between the mixing impeller and the motor which drives the mixing impeller. In other words, the method may be used for reusable or single-use mixing vessels, may be used for flexible or rigid mixing vessels, and may be used for mixing impellers which are connected with the motor via a driving shaft extended through a side wall of the mixing vessel or a mixing impeller which is magnetically connected to a motor.

The mixing impeller is rotated at the speed $N_{start}$. The speed $N_{start}$ is specified and is preferably a low speed. The term "low" means in this respect a speed which is lower than the speed at which the mixing is usually operated when mixing components.

If an overload is detected at speed $N_{start}$ and/or a higher torque than usual is detected at speed $N_{start}$, an alert may be sent to the operator informing the operator about the blocked mixing impeller. Additionally or alternatively, a startup operation of the mixing impeller may be blocked, the mixing impeller may be rotated at a low speed for a specified time, the mixing impeller may be rotated at speed $N_{start}$ until solids are no longer detected, the mixing impeller may be intermittently rotated, and/or the mixing impeller may be rotated in an opposition rotation direction.

According to a further aspect of the disclosure, the underlying technical problem has been solved by a method for detecting settled solids at a mixing impeller, comprising:

providing the mixing impeller in a mixing vessel, wherein the mixing impeller comprises a mixing impeller housing which houses at least one magnet and at least one mixing blade attached to the mixing impeller housing, wherein the mixing impeller housing is at least partly arranged in a mounting depression in a side wall (particularly a bottom surface and/or a lateral surface) of the mixing vessel, wherein the at least one magnet is magnetically connected to a motor to be driven;

accommodating components to be mixed in the mixing vessel;

rotating the mixing impeller such that mixing impeller housing is levitating in the mounting depression;

moving the mixing impeller in a direction having a movement component substantially perpendicular to a rotation axis of the mixing impeller so that a gap between the mixing impeller housing and the mounting depression reduces; and determining that mixing impeller is blocked by solids if the mixing impeller has not moved the specified distance.

This method only applies for mixing systems in which a motor being bearingless is used for driving the mixing impeller. Only such motors have the capability of measuring and adjusting the radial position of the at least one magnet in the mixing impeller.

The mixing impeller housing in which the at least one magnet is accommodated is at least partly arranged in a mounting depression of a mixing vessel so that the motor preferably a circumferential access to the magnet(s) contained inside of the mixing impeller.

In the case that solids are settled into the space between the mixing impeller housing and the mounting depression, the resulting friction may prevent the mixing impeller from starting or it could generate particulate by grinding against the walls of the mixing impeller and the mounting depression.

The described detection of solids is able to determine whether the mixing impeller is blocked by solids so that any damages at the mixing impeller and/or mixing vessel can be prevented.

The method may further comprise the steps of:
returning the mixing impeller to its original position;
moving the mixing impeller in a different direction having a moving component substantially perpendicular to the rotation axis; and
again determining that the mixing impeller is blocked by solids if the mixing impeller has not moved the specified distance.

The original position of the mixing impeller refers to the position at which the mixing impeller has been rotated at beginning of the method when starting the mixing impeller to rotate.

These and other objects, features and advantages of the present invention will become more evident by studying the following detailed description of preferred embodiments and the accompanying drawings. Further, it is pointed out that, although embodiments are described separately, single features of these embodiments can be combined for additional embodiments.

DETAILED DESCRIPTION

In the following the disclosure is described with reference to particular embodiments.

When mixing components such as two or more components in a mixing vessel, it is often important to monitor and/or determine a flow behaviour of mixed components being mixed by an impeller of a specific (predetermined or predeterminable) configuration, such as a Rushton impeller, within the mixing vessel having also a specific (predetermined or predeterminable) configuration. In a method of monitoring a flow behaviour of mixed components according to a particular embodiment of the invention use particularly is made of a Reynolds number $N_{Re}$ of the system (particularly corresponding to the specific impeller type and/or geometry used) and a Power number $N_P$ relative to a power applied to the impeller to rotate the impeller at a specified (predetermined or predeterminable) speed N.

The Reynolds number $N_{Re}$ particularly is a dimensionless number used in fluid dynamics to characterize the relative impacts of inertial forces and viscous forces in a fluid. For mixing applications, the Reynolds number may be defined as follows:

$$N_{Re} = \frac{\rho N^2 D}{\mu}$$

Here, $\rho$ is the density of the liquid (kg/m3), N is the speed at which the mixing impeller is rotated (rotations per second), D is the diameter of the mixing impeller (m), and $\mu$ is the dynamic viscosity of the liquid (m2/s).

Further, the Power number NP is another dimensionless number used to relate the power required to rotate a mixing impeller, the fluid density, the speed of the mixing impeller and the diameter of the mixing impeller. The Power number $N_P$ is as follows:

$$N_P = \frac{P}{\rho N^3 D^5}$$

Here, P is the power (watts) required to rotate the mixing impeller, $\rho$ is the density of the liquid (kg/m$^3$), N is the speed at which the mixing impeller is rotated (rotations per second), and D is the diameter of the mixing impeller (m).

The Reynolds number $N_{Re}$ and the Power number $N_P$ may be related for any specific mixing system geometry (specific mixing impeller geometry and/or mixing vessel geometry). At low Reynolds numbers $N_{Re}$ (usually below about 10 s$^{-1}$, due to low speed or high viscosity), the flow of the components to be mixed is laminar and the Power number $N_P$ changes as a function of speed. Accordingly, the Power number $N_P$ is considered to be $N_{P,variable}$ in this range. At a high Reynolds number $N_{Re}$ (usually above 500, e.g. due to high speed and low viscosity), the flow is turbulent and the Power number $N_P$ becomes constant, i.e. independent of fluid viscosity. Accordingly, the Power number $N_P$ is considered to be $N_{P,constant}$ in this range. Between the laminar and turbulent portions a transitional portion is present. It is preferred to mix in the turbulent portion where possible.

Figure 1A:
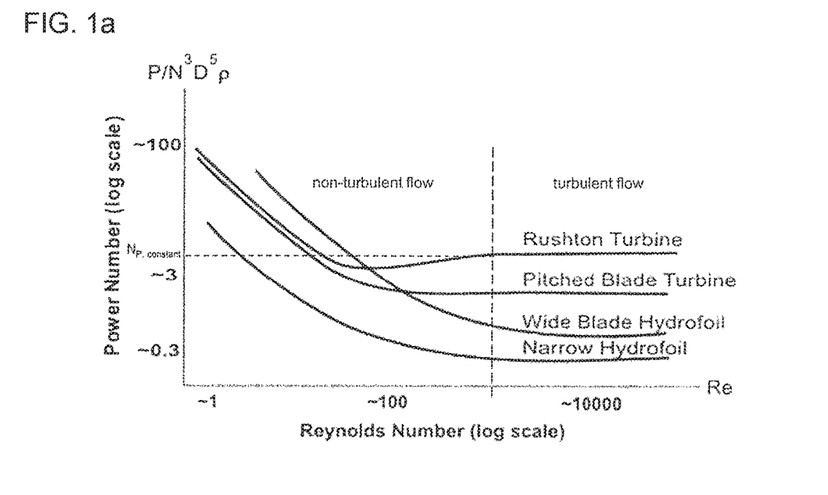
FIG. 1a shows a first diagram indicating the relationship between the Power number $N_P$ and the Reynolds number $N_{Re}$.
Figure 1B:
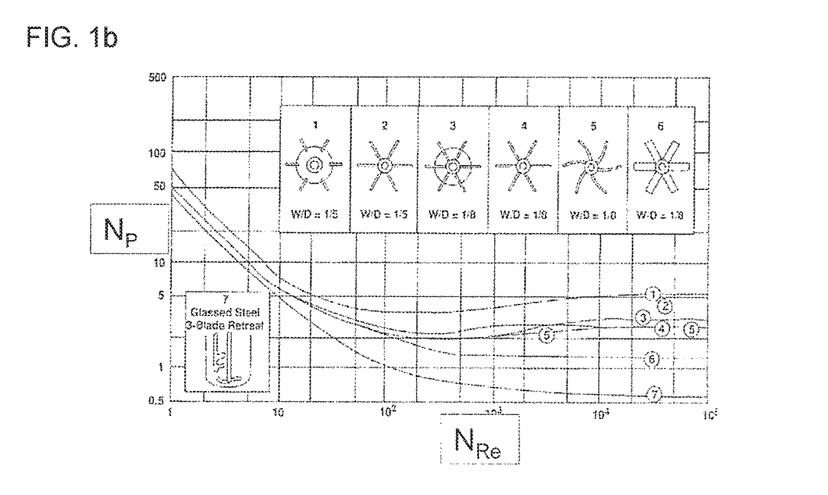
FIG. 1b shows a second diagram indicating the relationship between the Power number $N_P$ and the Reynolds number $N_{Re}$.

FIGS. 1a) and 1b) disclose exemplary diagrams in which the above described relationship between the Reynolds number $N_{Re}$ (see y-axis) and the Power number $N_P$ (see x-axis) are shown. In FIG. 1a) the relationship is disclosed for a Rushton Turbine, a Pitched Blade Turbine, a Wide Blade Hydrofoil Impeller and a Narrow Hydrofoil Impeller as published by Harnby et al. (1992). In FIG. 1b) a further exemplary diagram is shown indicating the relationship between Power number $N_P$ and the Reynolds number $N_{Re}$ for six different mixing impellers. The geometry of the respective mixing impellers is shown in the boxes 1 to 6 at the diagram being taken from Handbook of Industrial Mixing (First Edition, p. 361). In FIG. 1a), it is further indicated by a dashed line where the flow of mixed components is turbulent or non-turbulent as described above.

The explained relationship between the Power number $N_P$ and the Reynolds number $N_{Re}$ is used in the method according to the embodiment of the present invention in order to determine the density $\rho$ and the dynamic viscosity $\mu$ of mixed components. The displayed relationship between the Power number $N_P$ and the Reynolds number $N_{Re}$ may be stored in a memory and/or database for any specific mixing system geometry (particularly specific mixing impeller geometry and/or mixing vessel geometry) being of interest or used, e.g. as a look-up table, as a functional relationship (e.g. obtained by numerically fitting the respective curve(s) and/or analytically describing the respective correspondence).

Figure 3:
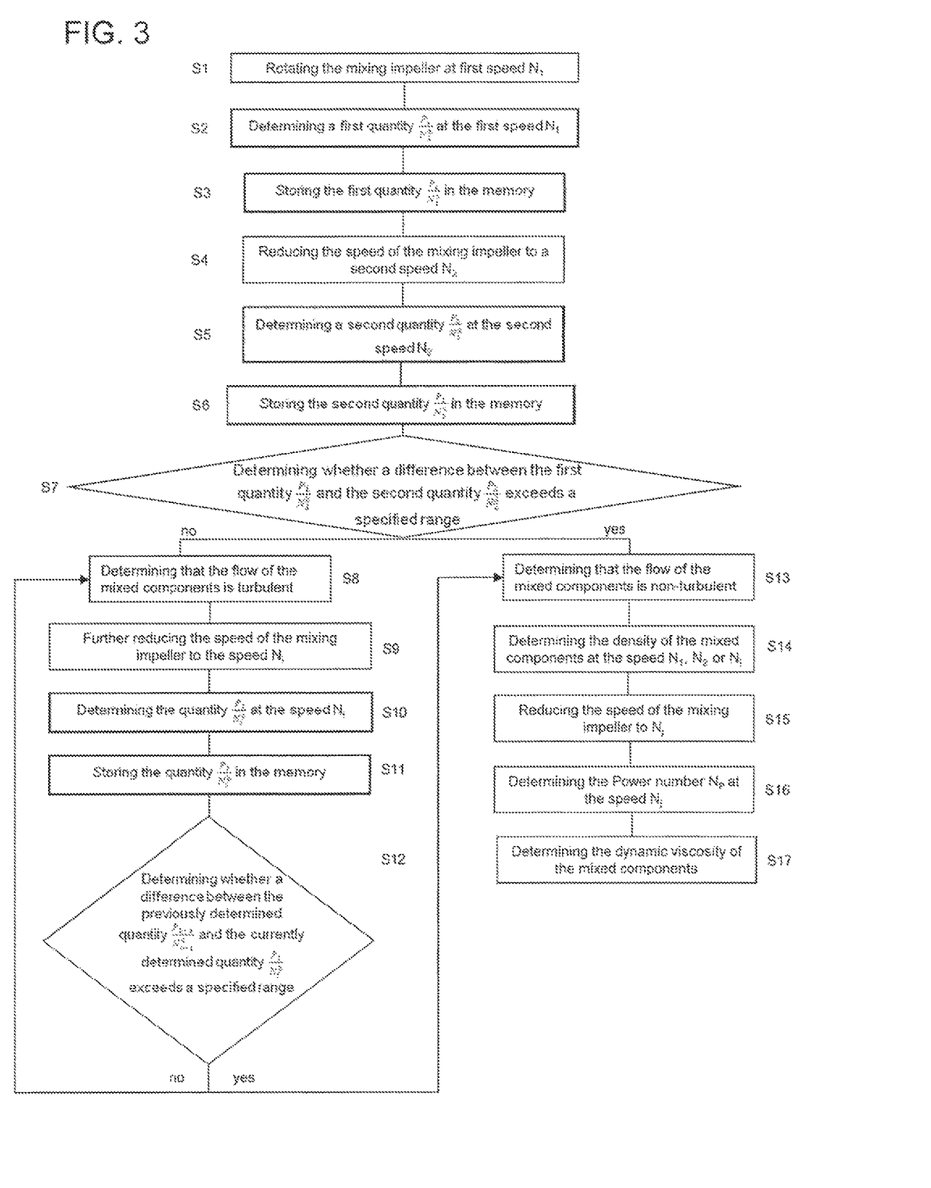
FIG. 3 shows a flow chart of the method of monitoring a flow behavior of mixed components.

FIG. 3 shows an exemplary flow chart corresponding to a particular embodiment of the invention.

The two or more components to be mixed (also referred to as mixing components) are accommodated in a mixing vessel. In the mixing vessel at least one mixing impeller is arranged, which is adapted to mix the components when being rotated. The mixing vessel may have a specific (predetermined or predeterminable) configuration, e.g. including one or more baffles, having a non-round cross-section and/or other specific properties. In particular, the mixing impeller within the mixing vessel may carry out mixing applications like e.g. homogenizing (compensation of concentration differences of different miscible components), liquid/liquid dispersing (stirring in of an insoluble medium into another fluid), liquid/gaseous dispersing (stirring in of gaseous phase into a liquid phase), suspending (swirling up and mixing of solids in a liquid phase), and emulsifying (stirring in of a liquid phase into a second liquid). It should be understood that the method of monitoring and/or controlling a flow behaviour of two or more mixed components according to the particular embodiment of the invention may be applied in connection with any type of the above mixing.

Initially, the mixing impeller is rotated by means of a drive device (such as a magnetically coupled driving device) at a first speed $N_1$ (Step S1). The first speed $N_1$ corresponds to a starting speed, which in specific circumstances may be or correspond to the highest speed at which the mixing impeller is or can be rotated e.g. in connection with this method. Preferably, the first speed $N_1$ is specified in a control system and/or may be input by a user. Here the first speed $N_1$ specifically may be stored. In particular, the first speed $N_1$ may be e.g. determined based on the carried out mixing application. The first speed $N_1$ particularly is indicated as $N_{max}$ in FIG. 2.

At this first speed $N_1$ a first quantity $$\frac{P_1}{N_1^3}$$

is determined (Step S2), wherein $P_1$ is the power (watts) required to rotate the mixing impeller at speed $N_1$ and $N_1$ is the speed at which the mixing impeller rotates. This determined first quantity $$\frac{P_1}{N_1^3}$$

particularly is stored in a memory (Step S3).

Figure 2:
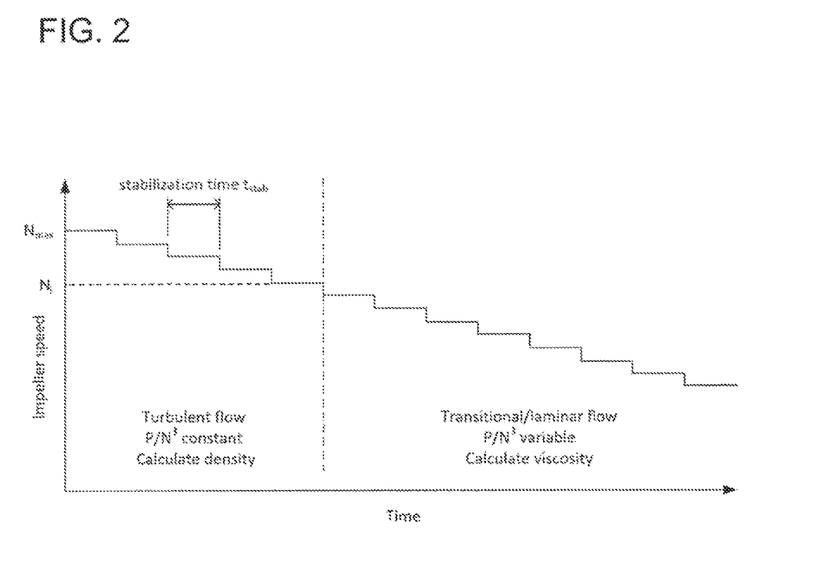
FIG. 2 shows a diagram indicating stepwise speed reduction of the mixing impeller according to the method of monitoring a flow behavior of mixed components.

Afterwards (Step S4), the speed of the mixing impeller is reduced to a second speed $N_2$ which is lower than speed $N_1$. Preferably, the speed is reduced at such a slow pace and/or maintained substantially constant during a time $t_{stab}$ that a flow pattern is allowed to stabilize. At this second speed $N_2$ a second quantity $$\frac{P_2}{N_2^3}$$

is determined (Step S5), wherein $P_2$ is the power (watts) required to rotate the mixing impeller at speed $N_2$ and $N_2$ is the speed at which the mixing impeller rotates. In FIG. 2, the second speed $N_2$ particularly corresponds to the second speed step starting from the left side in the diagram. The difference between first speed $N_1$ and the second speed $N_2$ may be specified (in a predetermined or predeterminable manner) in the control system and may depend on the specific type of mixing application carried out. The determined second quantity $$\frac{P_2}{N_2^3}$$

particularly is also stored in the memory (Step S6).

As shown in FIG. 2, the speed N particularly may be reduced stepwise, wherein the time for which the mixing impeller rotates at the respective speed N is $t_{stab}$. This time may be specified and preferably refers to the time within which the flow pattern is allowed to substantially stabilize. Preferably, and as shown in FIG. 2, the time $t_{stab}$ is identical for each step. It is, however, also possible that the time $t_{stab}$ is specified as being different for the various speeds $N_i$ and/or $N_j$.

In Step S7, a difference between the first and second quantities $$\frac{P_1}{N_1^3}, \frac{P_2}{N_2^3}$$

is determined. If the difference between the first and second quantities $$\frac{P_1}{N_1^3}, \frac{P_2}{N_2^3}$$

is within a specified range (i.e., $$\left| \frac{P_1}{N_1^3} - \frac{P_2}{N_2^3} \right| \leq T,$$

wherein T is a specified (predetermined or predeterminable) threshold value), the flow of the components to be mixed is considered (or determined) to be turbulent. If the difference between the first and second quantity extends beyond the specified range $$\left( \text{i.e.,} \left| \frac{P_1}{N_1^3} - \frac{P_2}{N_2^3} \right| \leq T \right),$$

the flow or the components to be mixed is considered (or determined) to be laminar and non-turbulent.

Provided that the difference between the first and second quantities does not exceed the specified range (no in Step S7), the flow of the mixed components is considered to be turbulent (Step S8). In this case, the speed of the mixing impeller is further reduced to speed $N_3$ (i.e. $N_3<N_2$) (Step S9) for which the third quantity $$\frac{P_3}{N_3^3}$$

is determined (Step S10). This third quantity $$\frac{P_3}{N_3^3}$$

particularly is again stored in the memory (Step S11). Afterwards, a difference between the previously determined second quantity and the currently third quantity is determined (Step S12). If the difference between the second and third quantities is within the specified range (similar to above Step S7), the flow of the components to be mixed is still considered (or determined) to be turbulent so that the flow returns to Step S8. This procedure is repeated in a corresponding manner as long as the flow of the mixed components is considered (or determined) to be turbulent (i.e. Steps S8 to S12 are iteratively repeated). Therefore, in Steps S9 to S12 the speed as well as the quantity are indicated by the index i, wherein i could be 3, 4, 5, 6, 7, etc. Especially the index i is intended to express that the flow of the mixed components is still considered (or determined) to be turbulent.

Provided that the determined difference between the first and second quantity or any difference between a previously determined quantity and a currently determined quantity exceeds the specified range (yes in Step S7 or S12), the flow of the mixed components is considered (or determined) to be non-turbulent (Step S13). If this has been determined, the density ρ of the mixture of components or components to be mixed is be calculated (Step S14) at a speed $N_i$ where the flow is determined to be turbulent by:

$$\rho = \frac{P_i}{N_{P,constant} N_i^3 D^5}$$

The formula is based on the formula for calculating the Power number $N_P$ as described above but is now dissolved for the density ρ.

The determination of the density ρ is determined for a speed $N_i$ where the flow is considered to be turbulent. In the formula, the Power $P_i$, the speed $N_i$ and the diameter D of mixing impeller are known. The Power number $N_{P,constant}$ can be taken or deduced from the known relationship between the Power number $N_P$ and the Reynolds number $N_{Re}$ (see FIG. 1, where $N_{P,constant}$ is indicated for a Rushton type impeller) for the specific mixing system geometry used. As the flow is considered or determined to be substantially turbulent, it is known that the Power number $N_P$ is constant as described above. Accordingly, the value of the Power number $N_P$ can be taken or deduced from the known relationship between the Reynolds number $N_{Re}$ and the Power number $N_P$ as particularly given or determined or stored for the specific mixing system geometry from the range where the Power number $N_P$ is constant. As mentioned, in FIG. 1a), $N_{P,constant}$ is exemplarily indicated for the Rushton Turbine type impeller.

The density ρ may be determined at any speed $N_i$ at which the flow is considered to be turbulent. In other words, the determination of the density ρ may be done e,g, after Step S3 or S5 or S10 and particularly stored. However, it is also possible to determine the density at different speeds $N_i$ at which the flow is considered or determined to be turbulent and use an average of the determined densities. In this case the average density $\bar{\rho}$ is calculated based on plural densities $\rho_n$ determined for plural speeds $N_n$ for which the flow is determined to be turbulent (i.e. n=1 . . . i), according to $$\bar{\rho} = \sum_{n=1}^{i} \frac{\rho_n}{i}$$

The determined density ρ (or average density $\bar{\rho}$) can be used for any of the following steps. Provided that the density ρ (or average density $\bar{\rho}$) could not be determined by means of the above described step or alternatively, the density may be input (like e.g. 1000 kg/m³ for water) by e.g. the operator.

FIG. 2 specifically shows five speed steps at which turbulent flow is detected/determined (left side of the dashed line). Preferably, at each of these steps the quantity $$\frac{P}{N^3}$$

may be determined.

Afterwards, the speed of the mixing impeller is further reduced to the speed $N_j$ (Step S15). The index j is intended to indicate speeds of the mixing impeller where non-turbulent flow appears in the mixed components. As shown in FIG. 2 at the right side of the dashed line, the speed is reduced stepwise. Preferably, the time for which the mixing impeller rotates at the respective speed $N_j$ particularly is $t_{stab}$. This is the time may be specified and preferably refers to the time within which the flow pattern is allowed to stabilize. Preferably and as shown in FIG. 2, the time $t_{stab}$ identical for is each step at least for the speed steps at the right side of the dashed line.

At least (or for) at one speed $N_j$, at which non-turbulent flow is determined, the Power number $N_{P,variable}$ is determined (Step S16):

$$N_{P,variable} = \frac{P_j}{\rho N_j^3 D^5}$$

The formula corresponds to the formular used to determine the Power number. The density ρ (or average density $\bar{\rho}$) has been determined previously as described above. The Power $P_j$ which is required to rotate the mixing impeller at speed $N_j$ and the speed $N_j$ at which the mixing impeller rotates are detectable. The diameter D of the mixing impeller is specified. The determined Power number is considered to be inconstant, as the Power number belongs to a flow where the flow is substantially non-turbulent. In this range, the Power number is no longer constant as described above. This range corresponds to the portion at the left side of the dashed line in FIG. 1a) for example for the Rusthon Turbine type impeller.

The dynamic viscosity μ is determinable afterwards (Step 17) on the basis of the following formula:

$$\mu = \frac{\rho N_j^2 D}{N_{Re}}$$

The formula is based on the formula for determining the Reynolds number $N_{Re}$ as described above, but dissolved for the dynamic viscosity μ.

The Reynolds number $N_{Re}$ is determinable on the basis of the calculated Power number $N_P$ at the speed $N_j$ as there is the described relationship between the Power number $N_P$ and the Reynolds number $N_{Re}$. Accordingly, when replacing the Reynolds number $N_{Re}$ in the formula by $x_T * N_P$, the following formula is achieved:

$$\mu = \frac{\rho^2 N_j^5 D^6}{x_T P_j}$$

It should be understood that the parameter $x_T$ particularly may take different values for different Reynolds numbers $N_{Re}$ e.g.

$x_T$ may take a value of approximately 0 when the flow is substantially turbulent (i.e. the Power number $N_{p,constant}$ will be constant for different Reynolds numbers $N_{Re}$), $x_T$ may be substantially constant for a laminar flow (i.e. for small Reynolds numbers $N_{Re}$, and $x_T$ may be variable, i.e. $x_T$ is a function of the Reynolds number $N_{Re}$ for a transition region e.g. between turbulent flow and laminar flow.

This specific relationship between Power number $N_P$ and the Reynolds number $N_{Re}$ being expressed by $x_T$ and its specific behaviour can be clearly seen in FIGS. 1a) and 1b) and may be stored in a database (e.g. as a functional relationship and/or in the form of a look-up table).

The density ρ has been calculated previously. The speed $N_j$ at which the mixing impeller rotates is known at it has been detected and the diameter D of the mixing impeller is also specified. The term $x_T$ corresponds to the specified relationship between the Reynolds number $N_{Re}$ for the used mixing system configuration and the determined Power number $N_{P,variable}$. The term $x_T$ may be retrieved from the database specifying the relationship between Reynolds number $N_{Re}$ (for the used mixing system configuration) and the Power number $N_{P,variable}$. Thus, the dynamic viscosity μ may be determined for a specific speed $N_j$ in the non-turbulent range or may be calculated for a plurality of speeds $N_j$ in the non-turbulent range. An average of the thereby determined dynamic viscosities $\mu_j$ may be then considered as the dynamic viscosity p of the mixed components.

FIG. 2 exemplarily shows eight speed steps at which non-turbulent flow is determined. Preferably, at each of these the dynamic viscosity is determined as described above. In this case, an average may be determined based on the determined dynamic viscosity. The speed may be reduced until a specified (predetermined or predeterminable) minimum speed is reached.

It should be understood that although it has been described that the density and the viscosity of the mixed components are determined when reducing the speed of the mixing impeller, it is also possible that the speed of the mixing impeller is reduced (preferably stepwise) from a maximum speed to a minimum speed and that afterwards the density and the viscosity of the mixed components is determined.

Accordingly, a method is provided by which the density ρ and the dynamic viscosity μ of mixed components can be determined in any easy manner without any further instrumentations or sampling in view of monitoring and/or controlling a flow behaviour of mixing components.

Figure 4:
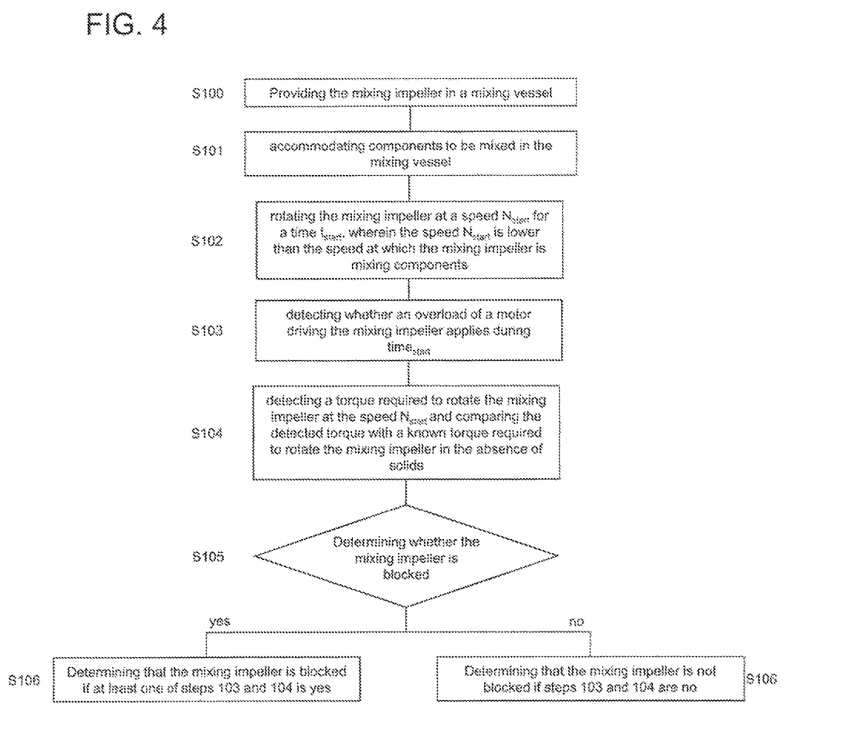
FIG. 4 shows a flow chart of a first embodiment of a method for detecting settled solids at a mixing impeller.

FIG. 4 shows a particular embodiment of a method for detecting settled solids at a mixing impeller.

In Step S100, a mixing impeller is arranged in a mixing vessel. Into this mixing vessel components to be mixed are inserted (step S101).

The mixing impeller is rotated at the speed $N_{start}$ (Step S102). The speed $N_{start}$ is specified by e.g. a control system and is preferably a low speed. The term "low" means in this respect a speed which is lower than the speed at which the mixing is usually operated when mixing components.

When the mixing impeller is rotating at the speed $N_{start}$, it is detected whether an overload occurs at the motor that drives the mixing impeller (Step S103).

Further, the torque that is required to rotate the mixing impeller at the speed $N_{start}$ is detected. This torque is compared with a torque which is usually required to rotate a mixing impeller at the speed $N_{start}$ when no solids are present in the mixed components (Step S104).

These detections are used to determine whether or not the mixing impeller is blocked by solids (Step S105).

If at least one of an overload and a torque required to rotate the mixing impeller at the speed $N_{start}$ being higher than torque usually required to rotate a mixing impeller at the speed $N_{start}$ when no solids are present is detected, it is determined that solids block the mixing impeller (Step S106). Otherwise, it is assumed that the mixing impeller is not blocked.

If an overload is detected at speed $N_{start}$ and/or a higher torque than usual is detected at speed $N_{start}$, an alert may be sent to the operator informing the operator about the blocked mixing impeller. Additionally or alternatively, a startup operation of the mixing impeller may be blocked, the mixing impeller may be rotated at a low speed for a specified time, the mixing impeller may be rotated at speed $N_{start}$ until solids are no longer detected, the mixing impeller may be intermittently rotated, and/or the mixing impeller may be rotated in an opposition rotation direction.

This method is generally applicable so that the method can be used for any kind of mixing impellers, mixing vessels and connections between mixing impellers and motors which drive the mixing impellers. In other words, the method may be used for reusable or single-use mixing vessels, may be used for flexible or rigid mixing vessels, and may be used for mixing impellers which are connected with the motor via a driving shaft extended through a side wall of the mixing vessel or a mixing impeller which is magnetically connected to a motor.

Figure 5:
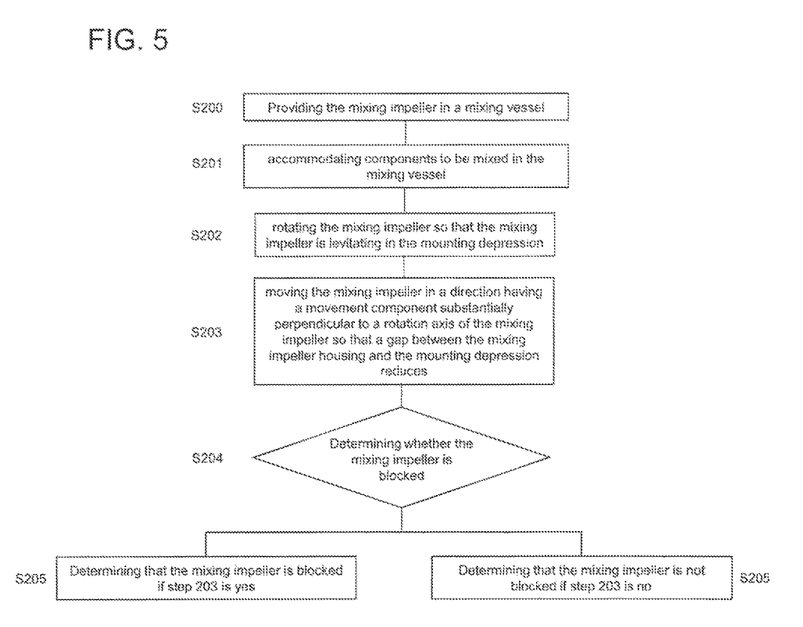
FIG. 5 shows a flow chart of a second embodiment of a method for detecting settled solids at a mixing impeller.

FIG. 5 shows another particular embodiment of a method for detecting settled solids at a mixing impeller.

A mixing impeller is provided in a mixing vessel (Step S200). The mixing impeller comprises a mixing impeller housing in which at least one magnet is accommodated. From the mixing impeller housing at least one mixing blade extends. The mixing impeller housing is arranged at least partly in a mounting depression of a mixing vessel so that the motor preferably has a circumferential access to the magnet(s) contained inside of the mixing impeller (Step S201). The mounting depression is provided in a side wall of the mixing vessel, and the side wall particularly may be a bottom surface of the mixing vessel or a lateral surface of the mixing vessel.

In the case that solids are settled into the space between the mixing impeller housing and the mounting depression, the resulting friction may prevent the mixing impeller from starting or it could generate particulate by grinding against the walls of the mixing impeller and the mounting depression.

The described detection of solids is able to determine whether the mixing impeller is blocked by solids so that any damages at the mixing impeller and/or mixing vessel can be prevented.

Preferably, the mixing impeller is rotated at low speed during the described method which is below the speed at which usually components are mixed. When rotating the mixing impeller the mixing impeller no longer rests on the bottom surface of the mounting depression but levitates in the mounting depression.

When rotating the mixing impeller (Step S202), the mixing impeller may be moved by a specified distance so that the gap between the mixing impeller and the mounting depression is reduced (Step S203). The direction may be perpendicular to the rotation axis of the mixing impeller and/or the rotation axis of the mounting depression. Alternatively, the direction has only a moving component which is perpendicular to the rotation axis of the mixing impeller and/or the rotation axis of the mounting depression. This means that the mixing impeller is moved laterally and upwards or downwards.

After this movement of the mixing impeller has been carried out, it is determined whether the mixing impeller is blocked by solids (Step S204).

If the specified (predetermined or predeterminable) distance by which the mixing impeller should move does not correspond to the distance by which the mixing impeller has been moved in fact, it is determined that the mixing impeller is blocked by solids. Otherwise, it is determined that the mixing impeller is not blocked (Step 205).

In order to check the previously made determination and/or in order to check whether the mixing impeller is not blocked by solids at another side of the mixing impeller, the mixing impeller may be moved to another direction also having a movement component perpendicular to the rotation axis of the mixing impeller and/or the rotation axis of the mounting depression. The direction is, however, different from the previous direction. Again it is determined whether the specified distance by which the mixing impeller should move corresponds to the distance by which the mixing impeller has been moved in fact in order to determine whether the mixing impeller is blocked by solids.

This method could be repeated as long as it is preferred.

This method applies, e.g., for mixing systems in which a bearingless motor is used for driving the mixing impeller. Such motors have the capability of measuring and adjusting the radial position of the at least one magnet in the mixing impeller.

What is claimed is:

1. A method of monitoring a flow behaviour of mixed components, comprising:
   rotating a mixing impeller at a first speed $N_1$ in a mixing vessel accommodating the components to be mixed;
   determining a first quantity $$\frac{P_1}{N_1^3}$$

at the first speed $N_1$, wherein $N_1$ is the speed at which the mixing impeller rotates and $P_1$ is the power required to rotate the mixing impeller at the first speed $N_1$;

decreasing the speed of the mixing impeller to a speed $N_2$;

determining a second quantity $$\frac{P_2}{N_2^3}$$

at the second speed $N_2$, wherein $N_2$ is the speed at which the mixing impeller rotates and $P_2$ is the power required to rotate the mixing impeller at the second speed $N_2$;

comparing the first quantity $$\frac{P_1}{N_1^3}$$

and the second quantity $$\frac{P_2}{N_2^3}$$

and detecting whether the difference between the first and second quantities is within a specified range to determine whether the flow of the components in the mixing vessel is a turbulent flow;

determining the density $\rho$ of the mixed components based on at least one speed $N_i$ for which the flow is determined to be turbulent by the following formula:

$$\rho = \frac{P_i}{N_{P,constant} N_i^3 D^5}$$

wherein $\rho$ is the density, $P_1$ is the power required to turn the mixing impeller at the speed $N_i$, $N_{P,constant}$ is the Power number for a used mixing system configuration, $N_i$ is the speed at which the mixing impeller rotates and $D$ is the diameter of the mixing impeller;

further decreasing the speed of the mixing impeller;

determining the Power number $N_{P,variable}$ for at least one detected speed $N_j$ at which the flow is determined to be non-turbulent by the following formula:

$$N_{P,variable} = \frac{P_j}{\rho N_j^3 D^5}$$

wherein $P_j$ is the power required to rotate the mixing impeller at the speed $N_j$, $\rho$ is the density previously determined based on $N_{P,constant}$, $N_j$ is the speed at which the mixing impeller rotates, and $D$ is the diameter of the mixing impeller; and determining the dynamic viscosity $\mu$ of the mixed components by the following formula:

$$\mu = \frac{\rho^2 N_j^5 D^6}{x_T P_j}$$

wherein $\rho$ is the calculated density, $N_j$ is the speed at which the mixing impeller rotates, $D$ is the diameter of the mixing impeller, $P_j$ is the power required to rotate the mixing impeller at the speed $N_j$ and $x_T$ corresponds to a specified relationship between the Reynolds number for the used mixing system configuration and the determined Power number $N_{P,variable}$.

2. The method of claim 1, wherein the current speed $N_i$ is iteratively reduced to a speed $N_{i+1}$ and the quantity $$\frac{P_{i+1}}{N_{i+1}^3}$$

is iteratively determined at the respective speed $N_{i+1}$ as long as a turbulent flow is determined when comparing the determined quantity $$\frac{P_{i+1}}{N_{i+1}^3}$$

with the previously determined quantity $$\frac{P_i}{N_i^3}.$$

3. The method of claim 1, wherein the average density $\bar{\rho}$ is calculated based on plural densities $\rho_i$ determined for plural speeds $N_i$ for which the flow is determined to be turbulent.

4. The method of claim 1, wherein the speed $N_i$ of the mixing impeller is reduced in steps and the speed $N_i$ is maintained for a specified time $t_{stab}$ so that a flow pattern is able to stabilize at each speed.

5. The method of claim 1, further comprising the step of outputting the determined density $\rho$ and the dynamic viscosity $\mu$.

* * * * *